(12) United States Patent
Schmaunz et al.

(10) Patent No.: US 10,347,461 B2
(45) Date of Patent: Jul. 9, 2019

(54) METHOD FOR THE IN SITU PREPARATION OF MICROSCOPIC SPECIMENS

(71) Applicant: Carl Zeiss Microscopy GmbH, Jena (DE)

(72) Inventors: Andreas Schmaunz, Oberkochen (DE); Holger Doemer, Bopfingen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 16/022,230

(22) Filed: Jun. 28, 2018

(65) Prior Publication Data

US 2019/0019650 A1 Jan. 17, 2019

(30) Foreign Application Priority Data

Jul. 13, 2017 (DE) .................. 10 2017 212 020

(51) Int. Cl.
*H01J 37/20* (2006.01)
*H01J 37/305* (2006.01)
(Continued)

(52) U.S. Cl.
CPC .......... *H01J 37/20* (2013.01); *H01J 37/3053* (2013.01); *H01J 37/3056* (2013.01); *H01J 37/31* (2013.01);
(Continued)

(58) Field of Classification Search
CPC ........ H01J 37/20; H01J 37/31; H01J 37/3056; H01J 37/3053; H01J 2237/28;
(Continued)

(56) References Cited

U.S. PATENT DOCUMENTS 8,912,490 B2 * 12/2014 Kelley ..................... G01N 1/32
250/306
2013/0143412 A1 6/2013 Moriarty et al.
(Continued)

FOREIGN PATENT DOCUMENTS

EP 1998356 A2 12/2008

OTHER PUBLICATIONS

Landefeld et al., "Nanoforging—Innovation in three-dimensional processing and shaping of nanoscaled structures," *Beilstein J. Nanotechnol.* 2014, 5, 1066-1070.
(Continued)

*Primary Examiner* — Michael Maskell
(74) *Attorney, Agent, or Firm* — Fish & Richardson P.C.

(57) ABSTRACT

A method relates to the in situ preparation of a microscopic specimen is carried out using a particle beam device, which includes a particle beam column for producing a focused beam of charged particles, a specimen receptacle for receiving a specimen block, and a detector for detecting interaction products of the interaction between particle beam and specimen material. The method includes: providing a specimen block having an exposed structure that comprises a specimen region of interest; producing a bending edge in the exposed structure by the action of the particle beam such that at least some of the exposed structure is shaped in the direction of the incident particle beam; and moving the specimen receptacle, in which the specimen block is received, so that a specimen region, which is enclosed by the shaped structure, is observable and/or processable in the particle beam device.

20 Claims, 11 Drawing Sheets

(51) Int. Cl.
*H01J 37/31* (2006.01)
*H01J 37/28* (2006.01)
*G01N 1/28* (2006.01)

(52) U.S. Cl.
CPC .............. *G01N 1/286* (2013.01); *H01J 37/28* (2013.01); *H01J 2237/063* (2013.01); *H01J 2237/08* (2013.01); *H01J 2237/28* (2013.01); *H01J 2237/2802* (2013.01); *H01J 2237/31745* (2013.01); *H01J 2237/31749* (2013.01)

(58) Field of Classification Search
CPC ..... H01J 2237/31749; H01J 2237/2802; H01J 2237/063; H01J 2237/08; H01J 2237/31745; H01J 37/28; G01N 1/286
USPC .................................. 250/306, 307, 310, 311
See application file for complete search history.

(56) References Cited

U.S. PATENT DOCUMENTS

2014/0061032 A1    3/2014  Miller et al.
2016/0141147 A1    5/2016  Brogden et al.

OTHER PUBLICATIONS

Giannuzzi et al., "FIB Lift-Out for Defect Analysis," Microelectronic Failure Analysis Desk Reference 2202 Supplement (2002).
Giannuzzi et al., "A review of focused ion beam milling techniques for TEM specimen preparation," Micron 30 (1999) 197-204.
Langford et al., "In situ lift-out: Steps to improve yield and a comparison with other FIB TEM sample preparation techniques," Micro 39 (2008) 1325-1330.
Langford et al., "Cantilever technique for a preparation of cross sections for transmission electron microscopy used a focused ion beam workstation," J. Vac. Sci Technol. B 18(1), Jan./Feb. 2000.
Tomus et al., "In situ lift-out dedicated techniques using FIB-SEM system for TEM specimen preparation," Micron 44 (2013) 115-119.
Lee et al., "Three-dimensional nanofabrication of polystyrene by focused ion beam," Journal of Microscopy 224 (2012) 129-139.
Jublot et al., "Sample preparation by focused ion beam micromachining for transmission electron microscopy imaging in front-view," Micron 56 (2014) 63-67.
German Office Action, with translation thereof, for corresponding DE Appl No. 10 2017 212 020.7, dated Oct. 31, 2017.

* cited by examiner

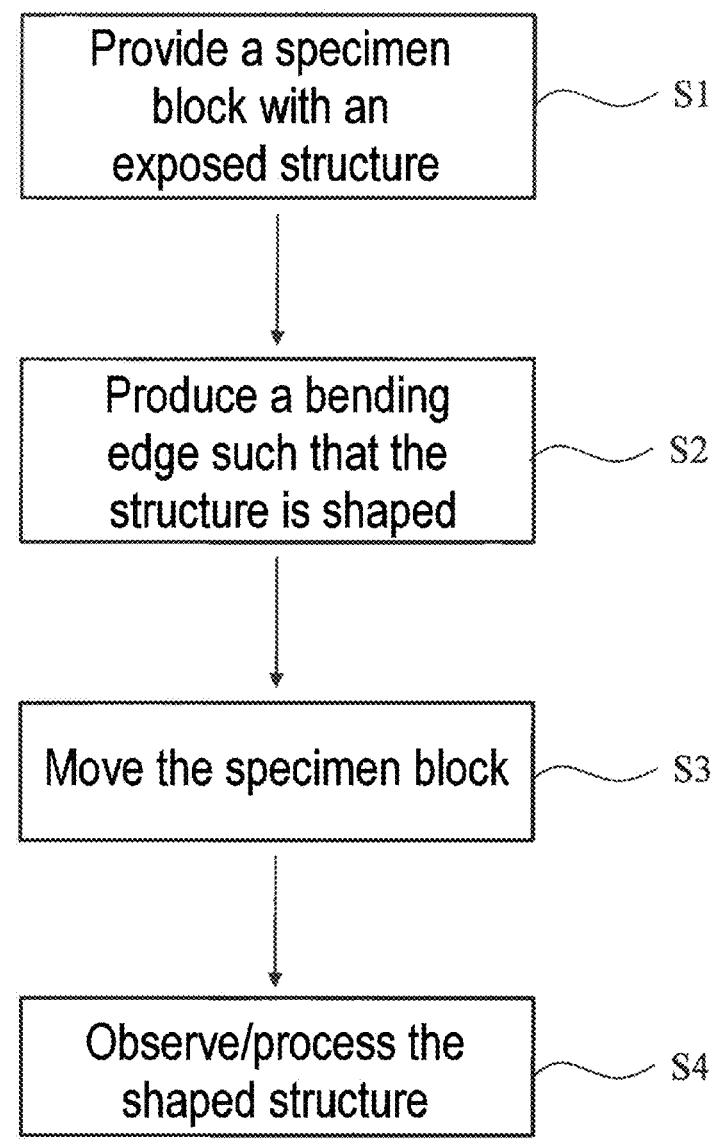

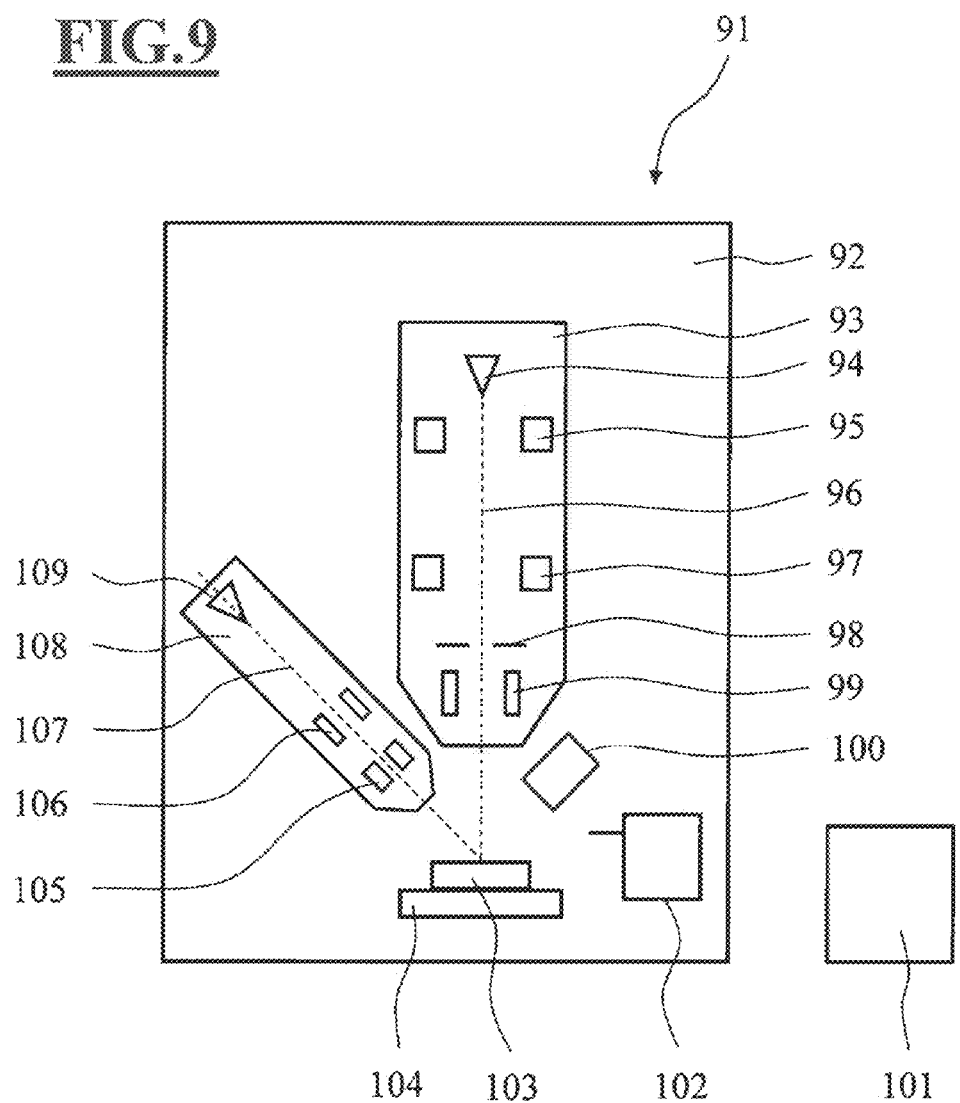

METHOD FOR THE IN SITU PREPARATION OF MICROSCOPIC SPECIMENS

CROSS-REFERENCE TO RELATED APPLICATION

This application claims benefit under 35 U.S.C. § 119 to German Application No. 10 2017 212 020.7, filed Jul. 13, 2017, the entire contents of which are hereby incorporated by reference.

FIELD

The disclosure relates to a method for the in situ preparation of specimens for an examination by electron microscopy, wherein the specimens are obtained from a specimen block. The electron microscopy specimen is shaped, and observed and/or processed, in a particle beam device by the action of a beam of charged particles.

BACKGROUND

Electron microscopy specimens (also referred to in short as microscopy specimens below) have dimensions that lie in the sub-millimeter range, i.e., in the range of a few micrometers (μm) or nanometers (nm). Usually, these specimens are examined in an electron microscope (scanning electron microscope or transmission electron microscope, TEM) or in an ion microscope or in other devices with a similar resolution.

Such specimens may have different configurations. An example of an often-used microscopic specimen is a TEM lamella, which is involved for transmission electron microscopy. TEM lamellas are so thin that, at least in portions, they are transmissive to electrons. Therefore, the electron-transparent specimen regions can be passed by electrons within the scope of the examination in the transmission electron microscope (TEM) such that transmitted electrons can be detected and used for image production purposes.

So that TEM lamellas contain the specimen region of interest (ROI), they are, in general, be prepared from the full specimen material, i.e., from a specimen block. The TEM lamella is severed and removed from the specimen block by way of a so-called lift out so that it is then examined in a different device, preferably a TEM.

In general, a distinction is made in the microscopic specimen preparation between ex situ methods and in situ methods, depending on the type of lift out.

In the case of an ex situ lift out, a specimen region of interest, which is still situated in the specimen block, is initially thinned using a focused ion beam (FIB) in an FIB device. That is to say, material is ablated with the ion beam until the specimen has the desired lamella thickness and said specimen is present as an electron-transparent lamella. Then, the ion beam is used to cut the side edges of the TEM lamella free such that the TEM lamella is largely exposed. In the next step, the entire specimen block, together with the TEM lamella, is removed from the FIB device and transferred into a light microscope. There, a glass tip is fastened to the TEM lamella with the aid of a micromanipulator. The TEM lamella can now be detached from the specimen block and transferred to a TEM grid or any other suitable specimen holder via the micromanipulator. The TEM grid with the TEM lamella is then transferred into the TEM for further examination.

In the case of the in situ lift out, the region of the future TEM lamella is initially freely prepared with the ion beam in broad brushes. The TEM lamella is released from the specimen block via a micromanipulator, which is attached to the FIB device, held in the specimen chamber of the FIB device and thinned to the desired lamella thickness by way of the ion beam. Finally, the TEM lamella is placed on a TEM grid or the like and fastened where desired, and it thus can be transferred from the FIB device into the TEM.

In the ex situ lift out, the specimen block is therefore situated outside of the FIB device when the microscopic specimen is severed from the specimen block, whereas this occurs within the FIB device in the in situ methods. What is common to both methods is that special manipulation tools such as micromanipulators, micro grippers or needles are involved.

Some methods additionally involve apparatuses for introducing process gases such that substances can be deposited in a targeted manner, said substances allowing the prepared microscopic specimen to be fastened to a glass tip or a metal needle, for example. Moreover, the user should have a certain amount of experience of handling the tools and experimental skill in order to successfully prepare the specimens within a justifiable amount of time.

Therefore, in many applications in electron microscopy and ion microscopy, it would be advantageous to be able to release selected small structures or specimen regions in a contactless manner from the specimen block from which they are obtained in order to thus make said small structures or specimen regions accessible to the further examination or processing.

Various methods of TEM lamella preparation are known. Thus, different types of FIB lift out techniques (ex situ and in situ) have been described for the defect analysis of wafers (Giannuzzi et al., 2002; Giannuzzi & Stevie, 1999).

Additionally, improved methods for the in situ lift out of TEM specimens with the aid of a two-beam device (Langford & Rogers, 2007; Tomus & Ng, 2013) are known.

EP1998356 A2 describes a method for an in situ STEM specimen preparation via an SEM-FIB combination device, which makes do without a flip stage.

Moreover, a method for the three-dimensional nano fabrication of thermoplastic polymers via FIB has been described.

Langford et al. (2000) disclose a cantilever technique for the TEM lamella production, in which the specimen block is removed from the FIB device in order to sever the prepared cantilever from the specimen block by the application of force.

Moreover, methods have been described for shaping microscopically small structures with micro and nano tools (so-called "nano forging").

The following documents should be considered:
EP 1998356 A2
Landefeld, A., Rösier J (2014): Beilstein J. Nanotechnol. 5: 1066-1070
Giannuzzi et al (2002): Microelectronic Failure Analysis Desk Reference 2202 Supplement
Giannuzzi & Stevie (1999): Micron 30: 197-204
Langford & Rogers (2007)
Langford et al. (2000): J. Vac. Sci Technol. B 18(1)
Tomus & Ng (2013): Micron 44: 115-119
Lee et al. (2012): Journal of Microscopy 224, 129-139

SUMMARY

The disclosure provides methods with which microscopic specimens can be shaped in a contactless manner and can be made accessible to further examinations. Moreover, the disclosure relates to the transfer of microscopic specimens by way of contactless shaping.

In one general aspect, the disclosure provides a method for in situ preparation of a microscopic specimen, carried out with the aid of a particle beam device including: a particle beam column for producing a focused beam of charged particles; a specimen receptacle for receiving a specimen block; and a detector for detecting interaction products of the interaction between particle beam and specimen material. The method includes: a) providing a specimen block having a structure that is exposed and that includes a specimen region of interest (ROI); b) producing a bending edge in the exposed structure by the action of the particle beam such that at least some of the exposed structure is shaped in the direction of the incident particle beam; and c) moving the specimen receptacle, in which the specimen block is received, in such a way that a specimen region, which is enclosed by the shaped structure, is observable and/or processable in the particle beam device.

In another general aspect, the disclosure provides a method for transferring a microscopic specimen, carried out with the aid of a particle beam device including: a particle beam column for producing a focused beam of charged particles; a specimen receptacle for receiving a specimen block; a detector for detecting interaction products of the interaction between particle beam and specimen material; and a displaceable transfer apparatus for receiving the microscopic specimen. The method includes: a) providing a specimen block having a structure that is exposed and that includes the specimen to be prepared; b) positioning the transfer apparatus; c) producing a bending edge in the exposed structure by the action of the particle beam such that at least some of the exposed structure is shaped in the direction of the incident particle beam, wherein the shaped structure is moved into the vicinity of the transfer apparatus; d) fastening the structure to the transfer apparatus; and e) severing the structure from the specimen block.

The present disclosure further relates to a computer program product which prompts a particle-optical apparatus to carry out a method according to the disclosure.

Moreover, the disclosure provides microscopic bending objects that have a plurality of bending edges and that are obtainable from one of the disclosed methods.

In a general aspect, the disclosure provides a microscopic specimen having a plurality of bending edges, obtainable according to a method disclosed herein.

Sometimes, microscopic specimens are prepared from the full specimen material, i.e., from a specimen block. Using the method according to the disclosure, a selected specimen region can be exposed from the specimen block in the particle beam device—i.e., in situ—, with the specimen region remaining connected to the specimen block. This is brought about by virtue of the specimen region being embodied as a cantilever that is folded out of the plane of the surface of the specimen block in a contactless manner. In this context, contactless means that the specimen region to be shaped does not come into direct contact with a shaping tool and it is not connected indirectly to such a tool either (for example, by depositing material or by accumulations on account of electric charges or other forces, such as van der Waals' forces, for example).

As a result of the contactless shaping, the microscopic specimen is deformed plastically—i.e., permanently. The deformation is possibly caused by electric charges and/or thermal effects, which trigger internal tensions. The specimen region of interest, which is situated in or at the cantilever-shaped structure, becomes accessible to further examinations or the further processing in the particle beam device by the shaping. An advantage of this method is that there is no need for holding tools such as a micromanipulator or glass needle. Moreover, preparation and observation or processing can be carried out in the same particle-optical device, and so the transfer between different devices, which is used in the known methods, can be dispensed with.

The method according to the disclosure is carried out in a particle-optical apparatus. This can be an ion beam microscope or a multi beam microscope (i.e., a combination device that includes at least two particle beam devices). By way of example, the apparatus can be embodied as a two-beam microscope (i.e., a combination device including an ion beam microscope and an electron beam microscope) or as an electron beam microscope with a gas injection system. It is also conceivable for the method to be carried out using a combination device, which includes an ion beam microscope and a light microscope. The particle beam device also can include an x-ray apparatus.

Using the method according to the disclosure, it is possible, for example, to produce TEM lamellas. TEM lamellas are ultra-thin specimens that are suitable for the examination in the transmission electron microscope since the lamellas are transparent to electrons, at least at points. This means that the specimen material of the TEM lamella can be traversed by electrons of an electron beam produced in the TEM. As a rule, TEM lamellas substantially have the form of a flat cuboid, the length and width of which are usually several micrometers (μm). The thickness (lamella thickness) of the cuboid is usually less than one hundred nanometers (nm), and so the lamella is electron- transmissive.

However, other specimen forms can also be prepared using the method according to the disclosure, said specimen forms having the form of a cylinder, a pyramid or a cone, for example. Such specimen forms are usually used for x-ray tomography or electron tomography.

Moreover, using a special embodiment of the method according to the disclosure, it is possible to transfer a microscopic specimen from the specimen block onto a transfer apparatus. By way of example, the transfer apparatus can be embodied as a micromanipulator needle or as a specimen holder.

Further, an embodiment of the disclosed method renders it possible to prepare electron- transparent specimens in situ and analyze these using a STEM (scanning transmission electron microscopy) detector.

According to further embodiment, it is possible to examine and image particles that lie on the surface of a specimen block. To this end, the particles are embedded in an applied coating. Subsequently, the deposition layer is shaped such that the particles fixed therein are lifted out of the plane of the specimen surface and able to be analyzed in the particle beam device.

Moreover, microscopic bending objects can be designed by contactless shaping using the method according to the disclosure. This occurs by virtue of cantilever-shaped structures being shaped by the action of a particle beam. Here, it is possible for the microscopic specimen produced to have two or more bending edges. Moreover, this allows different, three-dimensional microscopic bending objects to be produced.

BRIEF DESCRIPTION OF THE DRAWINGS

Exemplary embodiments are explained below on the basis of figures. Therefore, the entire respectively preceding and subsequent description is referred to as well for the purposes of explaining the components. In the drawings:

FIG. 1 is a flowchart of a method;

FIG. 9 schematically shows the structure of a two-beam device, which is suitable for carrying out a method.

EXEMPLARY EMBODIMENTS

Figure 2A:
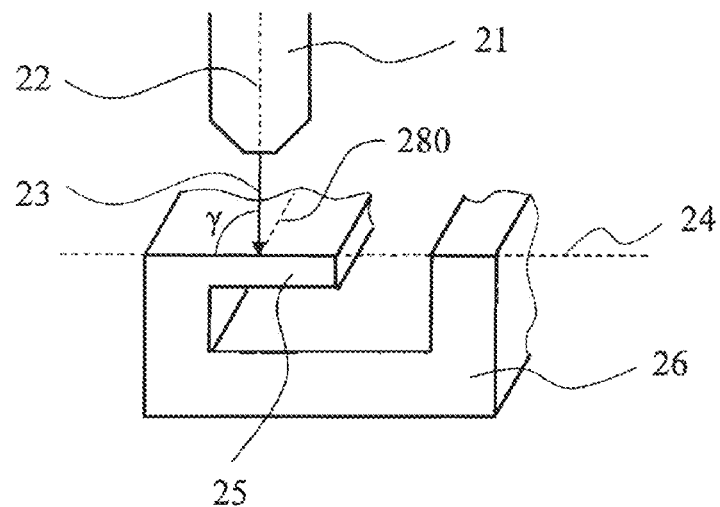
FIGS. 2A and 2B show the principle of a configuration of a method on the basis of an idealized sectional illustration of a specimen block (areal section)

FIG. 1 shows a flowchart of the method according to the disclosure, which is carried out in a particle beam device. A specimen block with an exposed structure is provided in step S1. To this end, the specimen block is advantageously held by a specimen receptacle in the specimen chamber of the particle beam device.

Various methods are conceivable for producing a specimen block with an exposed structure. After a region of interest (ROI) has initially been identified and its position in the specimen block has been determined, specimen material surrounding this region is removed. The material ablation can be carried out in many different ways, for example by virtue of so-called trenches being ablated using the ion beam (so-called milling) or by virtue of the material being ablated in a step-shaped manner. It is also conceivable to bring about the material ablation by electron-beam-induced etching. To this end, etching gas is guided into the vicinity of the specimen surface while the electron beam is directed onto the specimen site to be processed. Specimen material is removed by the interaction of etching gas and electron beam. The introduction of the etching gas and the irradiation with the electron beam is preferably performed simultaneously in order to obtain a higher etching rate and be able to process a specific specimen region in a targeted manner. Moreover, however, it is also conceivable to produce a suitable specimen block with an exposed structure by mechanical processing (by cutting with a microtome or ultra- microtome, for example), by laser processing or by other methods.

In any case, the region of interest (ROI) is exposed to such an extent that it is situated in or at a cantilever-shaped structure, which is referred to as an exposed structure. Thus, the exposed structure includes the specimen region which should be examined in more detail and which should be prepared as a microscopic specimen. The method steps described below are carried out using a specimen block that has been prepared in this way.

A bending edge is produced in step S2 by the action of a beam of charged particles. By way of example, the particle beam can be a beam of focused ions. The ion beam is guided over the exposed structure such that specimen material is ablated by milling and a bending edge arises. Alternatively, it is also conceivable for the beam to be an electron beam and the bending edge to be produced by electron-beam-induced etching. The exposed structure is shaped along the bending edge as a result of notching the bending edge, and so the exposed structure is moved into another spatial position.

Usually, the bending edge arises by virtue of specimen material being ablated along a straight line via the particle beam. The bending edge is produced in the exposed region of the cantilever. As a result, the exposed structure is bent along the bending edge such that the structure is moved out of the original plane into a plane that is arranged at an angle with respect to the original plane. Only so much material is ablated when the bending edge is produced that the shaping occurs without, however, the exposed structure being severed from the specimen block.

The disclosure is based on the surprising discovery that the observed shaping behavior of the microscopic specimen can be used for specimen preparation and for contactless specimen transfer. The inventors have determined that the proposed method can be carried out with exposed structures whose cantilever has a cross-sectional thickness in the range from several ten nanometers to several micrometers. By way of example, it is conceivable for the method according to the disclosure to be carried out with a typical TEM lamella with an area of 20 μm×2 μm and a thickness of approximately 1 μm, wherein the cross-sectional thickness of the cantilever, in which the bending edge is produced, can be between 0.1 μm and 2 μm.

The exposed structure is shaped by producing the bending edge in the direction toward the incident particle beam. The user can stop the shaping process by virtue of stopping the action of the particle beam. However, the shaping process can also be continued again if the particle beam acts on the bending edge again. Then, the exposed structure is shaped further in the direction of the incident particle beam. In this way, the user can determine the extent of the shaping.

In step S3, the specimen receptacle, on which the specimen block is received, is moved. This is preferably carried out by rotating the specimen receptacle together with the specimen block about an axis that extends parallel to the specimen surface. As a result, the region of interest, which of course is situated in or at the shaped structure, can be examined further in the particle beam device without having to sever the exposed structure from the specimen block to this end. Likewise, the specimen block need not be removed from the particle beam device. Since the exposed structure has been moved out of the body of the specimen block, the specimen region of interest is now accessible from outside of the specimen block and observable and/or processable in the particle beam device.

Optionally, the method can be carried out with the additional step S4, in which a specimen region in the shaped structure is observed and/or processed with the aid of the particle beam device. This can occur in situ, i.e., without a transfer of the specimen from the particle beam microscope into another apparatus being involved. By way of example, regions of the shaped structure can be imaged with the aid of a detector, which can be included by the particle beam device, wherein the interaction products of the interaction between particle beam and specimen material are detected and an image is produced. Here, the detector can be embodied as a secondary electron detector, as a backscattered electron detector, as an EBSD (electron backscatter diffraction) detector, as a cathodoluminescence detector, as an x-ray detector or as any other suitable detector. Moreover, it is possible to process the shaped structure in situ, for example by irradiation with a particle beam, i.e., ablate material locally or areally or deposit material.

In a particularly advantageous embodiment, the form of the bending edge is stabilized by depositing material. To this end, material (e.g., a Pt-containing layer) is applied to the bending edge by an introduction of process gas and—where desired—an activation by electron and/or ion beam irradiation. As a result, the trench that arose when milling the bending edge is filled, while the two areas adjoining the bending edge are connected to one another.

FIG. 2A shows cross-section of an exemplary specimen block 26, which includes an exposed structure 25. This is understood to be a structure in the form of a cantilever that only abuts, or is connected to, the specimen block at one side. It is particularly advantageous if the cantilever-shaped structure includes a specimen region of interest, i.e., that specimen region that should be examined in more detail.

In the present example, the cantilever has the form of a cuboid. This means that the exposed structure 25 has six boundary surfaces in this case, of which five are exposed, i.e., do not have an areal contact with the specimen block 26. The cantilever is only connected to the material of the specimen block 26 at one boundary surface or along one cuboid edge.

It is also conceivable for the exposed structure to initially have the form of a bridge, which still abuts the specimen block at two boundary surfaces or two edges. By ion beam milling or etching a separating line extending predominantly transversely to the longitudinal direction of the bridge, it is possible to divide the bridge-shaped structure into two cantilevers, via which it is then possible to carry out the method according to the disclosure. It is also conceivable for the cut angle not to be arranged exactly transversely (90°) to the longitudinal direction of the exposed structure but instead assume a different angle between 0 and 90°.

Furthermore, it is possible for the exposed structure to be embodied as a conductor track of an electronic component. By way of example, the exposed structure can be embodied in such a way that it can subsequently serve as a capacitor or as a micro-switch.

However, the method is not restricted to cuboid, exposed structures. In principle, it is conceivable also to shape other structures, such as, e.g., cylindrical or conical structures, or any other form that is only connected to the specimen block at one edge. This is helpful, in particular, when producing three-dimensional objects by the method according to the disclosure. It is also conceivable for assembled forms to be produced using the described method: By way of example, the exposed structure can be embodied as a cuboid, connected to which there is a cylindrical specimen region that includes the point of interest.

The specimen block 26 illustrated in FIG. 2A is held by a specimen receptacle (not illustrated), which is situated in the specimen chamber of a particle beam device. The particle beam device includes a particle-optical column 21, which has an optical axis 22.

During operation, charged particles are produced in the particle-optical column 21, said particles being accelerated and steered onto the specimen block 26 as a focused particle beam 23. In the process, the charged particles substantially move along the optical axis 22. The particle-optical column 21 has an observation and processing plane 24, which extends substantially perpendicular to the optical axis 22. This is advantageous in that the particle beam is incident on the specimen surface at an angle γ of approximately 90°. However, it is also conceivable for the angle γ, at which the particles are incident on the specimen, to deviate from 90° and equal less than 90° and more than 0°, for example, preferably 80° or 70°. Advantageously, a first boundary surface of the exposed structure 25 lies in the observation and processing plane 24, and so processing of the exposed structure 25 is made simpler.

In the method according to the disclosure, the focused particle beam 23 is now steered onto the first boundary surface of the exposed structure 25 in such a way that a bending edge 28 is produced. By way of example, this is implemented by virtue of the particle beam 23 being guided over the first boundary surface along a processing line 280 such that specimen material is ablated along this line 280. As a result, a bending edge 28 arises and the exposed structure 25 is shaped in the direction of the incident particle beam 23. This means that, after shaping, the first boundary surface of the structure 25 no longer lies in the observation and processing plane 24 but instead assumes an angle β in relation to the observation and processing plane 24 that deviates from zero.

The exposed structure is only shaped for as long as the particle beam acts on the bending edge. By deactivating or deflecting (so-called blanking) the particle beam, the shaping is also stopped. This renders it possible to halt the shaping process once the desired extent of shaping has been achieved. Thus, the user can predetermine the desired extent of the shaping of the exposed structure 25 and shape the exposed structure in a targeted manner by stopping the action of the particle beam and, where desired, allowing the particle beam to act again.

In other words: The user can determine the angle β that the shaped exposed structure 27 adopts in relation to the observation and processing plane 24.

At most, the angle β can assume the value of the angle γ, at which the particle beam 23 used for the shaping is incident on the specimen surface. This means that the exposed structure can, at most, be shaped up to the incident particle beam. However, the angle β achievable overall can be increased by displacing the specimen block and/or tilting the specimen block (i.e., by moving the specimen receptacle) and repeated reshaping.

In principle, the specimen region of interest can extend in a plane parallel to the first boundary surface of the specimen block (areal section) or in a plane that extends perpendicular to the first boundary surface (cross section).

Figure 2B:
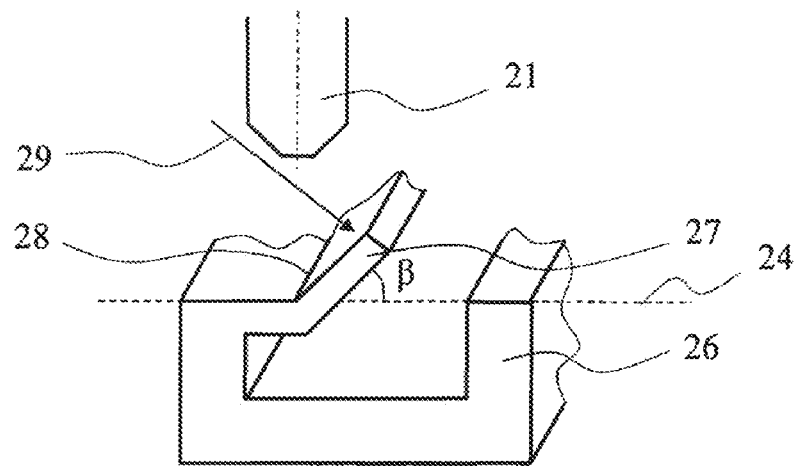

The example of FIG. 2A shows a specimen that was carved out as an areal section. For a further examination or further processing, the particle beam should be incident on the surface of the shaped structure 27 in approximately perpendicular fashion; i.e., the particle beam 29 should extend in the plane of the drawing as illustrated in FIG. 2B. To this end, the specimen receptacle with the specimen block can be displaced and/or rotated appropriately.

Figure 3A:
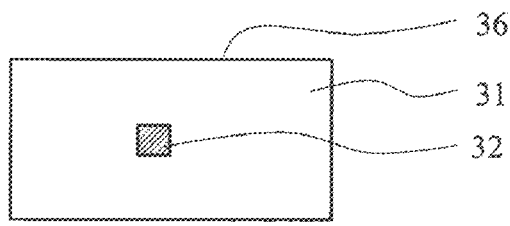
FIGS. 3A-3E show the principle of further configurations of a method on the basis of an idealized sectional illustration of a specimen block (cross section)
Figure 3B:
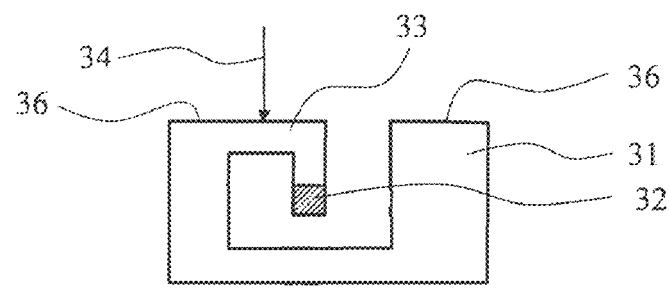
Figure 3C:
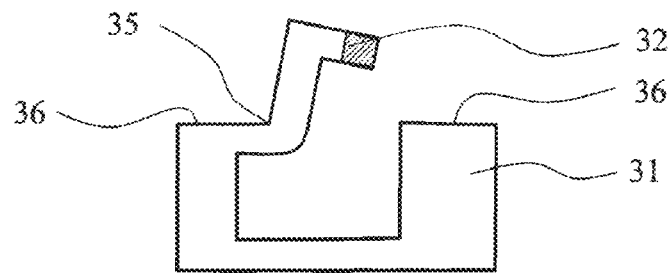

FIGS. 3A-3C illustrate how a cross section specimen is prepared. This is of particular interest to specimens that should be examined via STEM or TEM.

The cross section specimen allows lifting a specimen detail 32 of interest, which is buried in the interior of the specimen block 31, out of the volume of the specimen block 31 and making said specimen detail accessible to a further examination in the particle beam device. Here, the specimen detail 32 is initially identified in the interior of the specimen block 31 and an exposed structure 33 which includes the specimen detail 32 is prepared. A focused particle beam 34 is used to produce a bending edge 35 in the boundary surface 36 which lies in the focal plane of the particle beam 34, the specimen detail 32 rotating about said bending edge in the direction of the incident particle beam 34 during the shaping.

In the process, the exposed structure 33 is moved beyond the plane of the boundary surface 36 of the specimen block such that the specimen detail 32 is likewise moved beyond the plane of the boundary surface 36 and it is now possible to examine and/or process said specimen detail with the particle beam device. In the example of FIGS. 3A-3C, the areal extent of the specimen detail 32 of interest is mainly in a plane that extends perpendicular to the first boundary surface 36, i.e. perpendicular to the specimen surface. This means that the region of interest 32 represents a cross section of the specimen block, as is often the case in TEM lamellas, too.

In a particularly advantageous embodiment, the exposed structure 33 includes the specimen region which should be prepared as a TEM lamella and which is therefore embodied as a very flat cuboid. It is advantageous, during the subsequent examination or processing, if the particle beam is incident perpendicular onto the surface of the specimen detail 32, i.e., if the particle beam extends perpendicular to the plane of the drawing. To this end, the specimen receptacle with the specimen block can be displaced and/or rotated appropriately.

Figure 3D:
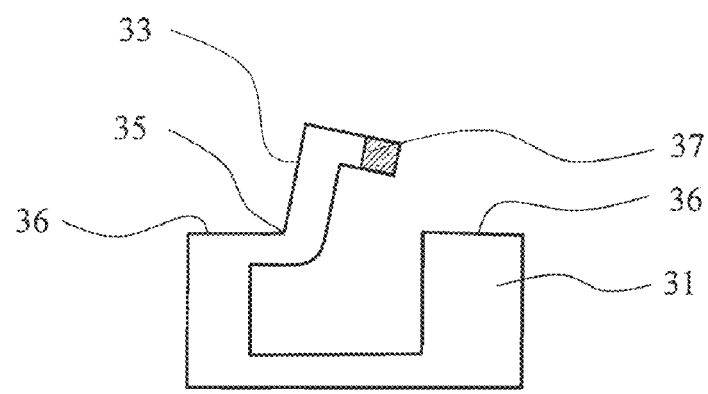
Figure 3E:
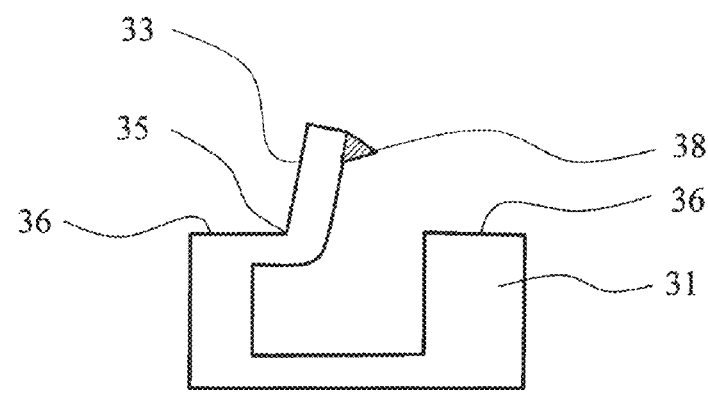

FIGS. 3D and 3E elucidate that the disclosed method also can be used to prepare tomography specimens for x-ray or electron tomography.

Reference signs 31, 33, 35 and 36 in this case have the same meaning as described in FIGS. 3A-3C. In order to prepare microscopic tomography specimens, the specimen detail of interest is prepared in such a way that it include a cylindrical structure 37 (FIG. 3D), which is connected to the cantilever-shaped exposed structure 33. Alternatively, the specimen detail of interest can also include a conical structure 38 (FIG. 3E). In any case, the exposed structure 33 is shaped by the described method such that the region to be examined by tomography is flapped out of the interior of the specimen block 31 and consequently accessible from outside of the specimen block 31. As a result, the tomography specimen is prepared in such a way that it can be processed and/or examined further in situ or can be transferred into another apparatus. What is advantageous in the case of preparing tomography specimens using the method according to the disclosure is that a cylindrical or conical structure (which is also referred to as a "pillar") is obtained, which can be penetrated from different sides for the purposes of a further examination without holding tools or a transfer into another apparatus being involved.

It is also conceivable to produce an adjustable capacitor using the method according to the disclosure. To this end, a specimen block including two cantilevers, which extend in parallel and which are embodied as conductor tracks, is provided. Said cantilevers each have a plate-shaped projection, said projections being able to serve as capacitor plates. The capacitance of the capacitor is determined by the distance of the two capacitor plates from one another and by the size of the effective area of the capacitive plates. The effective area is understood to be that area of a capacitor plate that interacts with the associated, oppositely charged capacitor plate (counter plate) in order to obtain the capacitor effect. By shaping at least one cantilever with a capacitor plate, the position of the capacitor plate is modified in relation to the counter plate, and so the effective area is modified. In this way, the capacitance of the capacitor is modifiable, and so the capacitor effect is adjustable. Alternatively, the capacitor can also have such an embodiment that the first capacitor plate is embodied as a cantilever while the second capacitor plate is formed by a wall surface of the specimen block.

In another embodiment, the capacitor is embodied as a cylindrical capacitor, i.e., in the form of two electrically conductive, concentric cylinder jackets. Here, the inner cylinder jacket is embodied as an exposed conductor track and connected to a cantilever. By producing a bending edge in the cantilever, it is possible to modify the position of the inner cylinder jacket, and so the length of the capacitor—and hence its capacitance—is modifiable. Consequently, this cylinder capacitor is also adjustable.

An electric micro-switch can be produced and operated with another embodiment of the method. Here, switching is brought about by a bending edge being introduced into a cantilever-shaped structure according to the disclosure in order to shape the structure such that the current flow via the switch is interrupted.

The entire exposed structure 25, 33 or only part of the exposed structure 25, 33 is shaped, depending on where the bending edge 28, 35 is produced along the longitudinal axis of the cantilever. Advantageously, the bending edge 28, 35 should extend near the support of the cantilever in order to shape the exposed structure 25, 33 as a whole. Moreover, it was found to be advantageous if the bending edge 28, 35 extends more or less perpendicular to the longitudinal axis of the exposed structure 25, 33. Preferably, the position and the profile of the bending edge are selected in such a way that the exposed structure 25, 33 does not contact the specimen block 26, 31 during shaping.

FIGS. 4A-4D shows, in an exemplary manner, another special configuration of the method according to the disclosure, in which the intention is to prepare a specimen block 41 which has particles 48 that should be examined in more detail situated on the surface thereof. By way of example, specimen block 41 includes silicon.

A coating 42, which includes platinum, for example, is applied onto the specimen block 41 via ion beam deposition (FIG. 4A) This coating 42 covers a layer of the silicon-containing specimen material situated therebelow and acts as a protective layer for the covered specimen region. The particles 48 lying on the specimen surface are embedded into the coating material. However, producing the coating is not restricted to depositing a platinum-containing layer. Rather, the coating can be effected by depositing other metals (e.g., tungsten) or by depositing carbon or other suitable substances. As an alternative to ion beam deposition, use can also be made of gas-assisted electron beam deposition.

The coating 42 is now prepared to be free (FIG. 4B) by virtue of being undercut in etching. This can be brought about via ion beam etching using xenon difluoride ($XeF_2$). Since $XeF_2$ is able to etch the specimen material even without the influence of the ion beam, the silicon under the platinum deposition is removed; i.e., the coating 42 remains freestanding and forms a bridge-like structure over the ablated region 43.

Figure 4A:
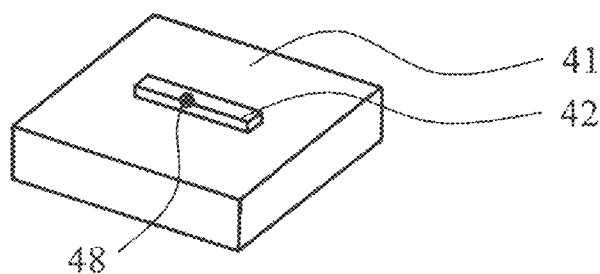
FIGS. 4A-4D schematically show steps of a configuration of a method.
Figure 4B:
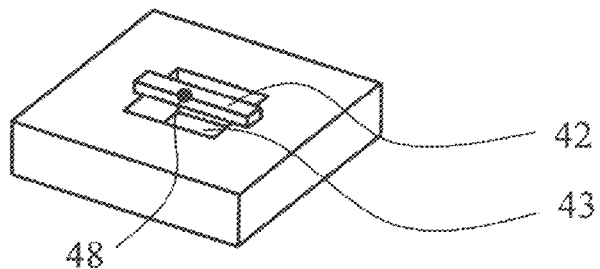
Figure 4C:
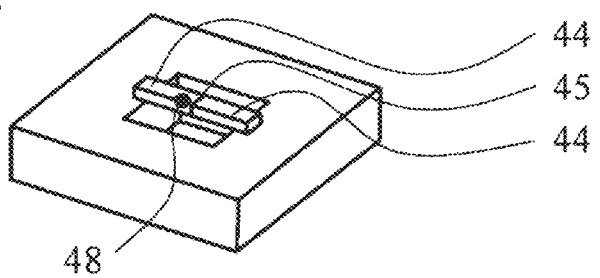

Now, the bridge-like coating 42 is cut with the aid of the ion beam (FIG. 4C). As shown in this example, this may be effected more or less centrally, and so two cantilevers of approximately the same size arise as exposed structures 44 by way of the severing cut 45.

Figure 4D:
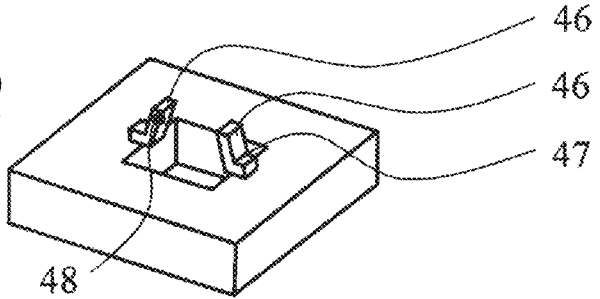

Then, the coating 42 is processed along a processing line by the particle beam such that small amounts of material are ablated and a bending edge 47 arises, at which the structure 44 is shaped (FIG. 4D). Therefore, the position of the processing line (and hence that of the bending edge 47) can be selected as desired within the exposed region. By way of example, a gallium ion beam with an acceleration voltage of 30 kV and a beam current of 50 pA can be used to produce the bending edge 47.

As a consequence of shaping, the exposed coating 42 folds in the direction of the incident ion beam, and so the deposition layer 42 with the particles 48 contained therein rotates about the bending edge 47 and said deposition layer is lifted out of the processing plane, and hence out of the plane of the specimen surface.

Here, too, shaping is effected slowly and it can be interrupted by deactivating or pivoting away (so-called "blanking") the ion beam. Shaping can be continued at a later time. As a result, the angle which the shaped structure adopts in relation to the observation plane of the particle beam device can be determined by the user. The maximum angle is restricted by the profile of the optical axis of the particle beam device; i.e., the deposition can be shaped at most so far that the structure reaches the trajectory of the incident ion beam.

The described shaping is repeated at the second cantilever, and so the specimen form shown in FIG. 4*d* arises.

Figure 5:
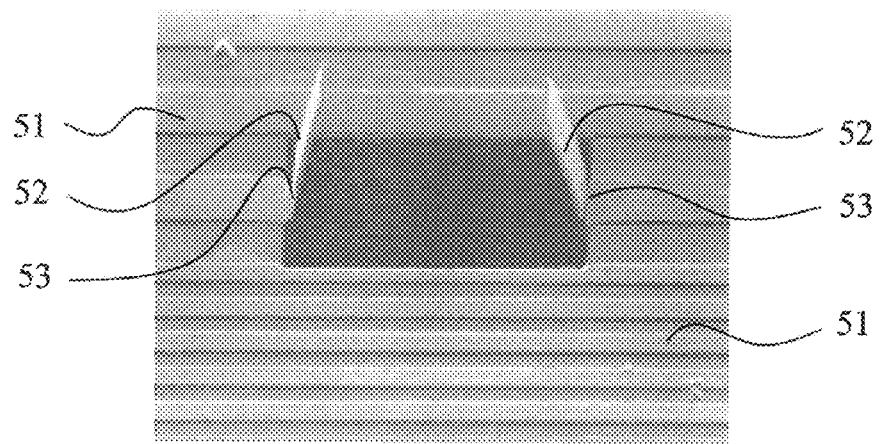
FIG. 5 reproduces an electron microscopic recording of a microscopic specimen produced using a method.

FIG. 5 shows the electron-microscopic image of a specimen block 51 that was prepared using the method according to the disclosure. The specimen block 51 contains silicon and was etched using $XeF_2$ in order to produce two exposed, gold-containing structures 52. The exposed structures 52 were shaped by producing bending edges 53.

Figure 6A:
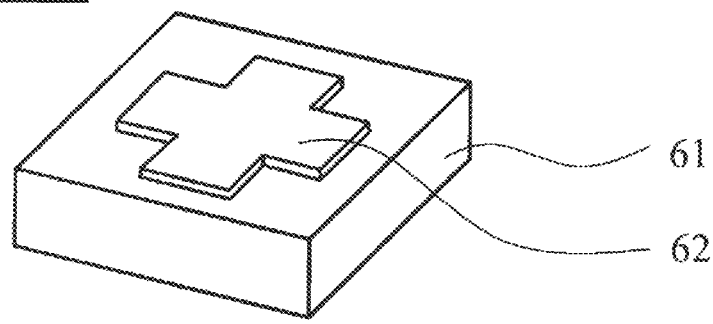
FIGS. 6A-6C show various steps during the production of a microscopic specimen, which is a three-dimensional bending object.
Figure 6B:
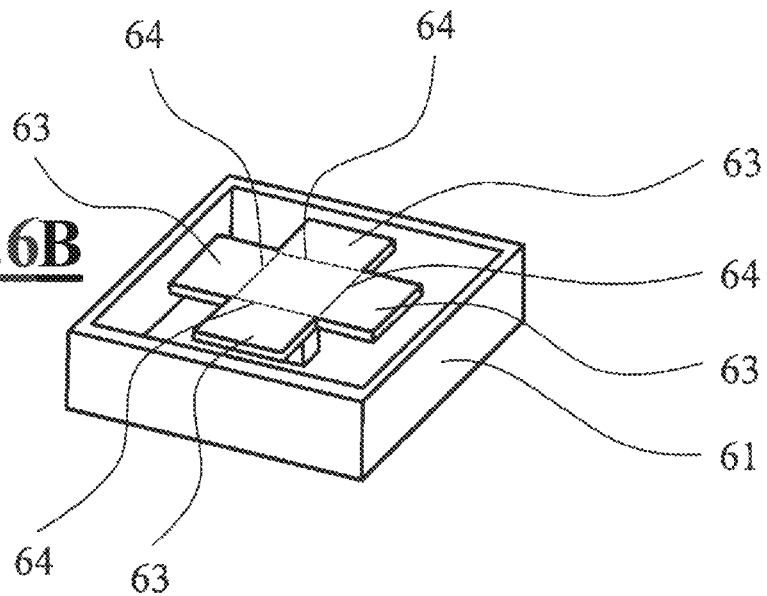
Figure 6C:
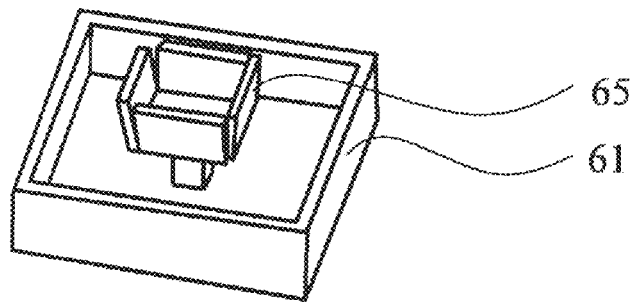

FIGS. 6A-6C schematically shows the production of a microscopic, three-dimensional bending object. Initially, a specimen block 61, which may include silicon, for example, is provided, an initial structure 62 having been deposited thereon. By way of example, this can be brought about by gas-induced ion beam deposition (e.g., of platinum-containing layers) or gas-assisted electron beam deposition.

Then, the initial structure 62 is undercut in etching, for example with $XeF_2$, in order to expose the initial structure 62. $XeF_2$ is able to etch silicon even without the influence of activating radiation, and so material can be ablated even at positions that cannot be irradiated directly by the particle beam. Four exposed cantilever structures 63 arise in this way in the present example. A bending edge 64 is produced at each of the exposed structures 63 by the action of the particle beam, and so the structures 63 are shaped. Hence, a three-dimensional object 65, which has a plurality of bending edges 64, arises.

Figure 7A:
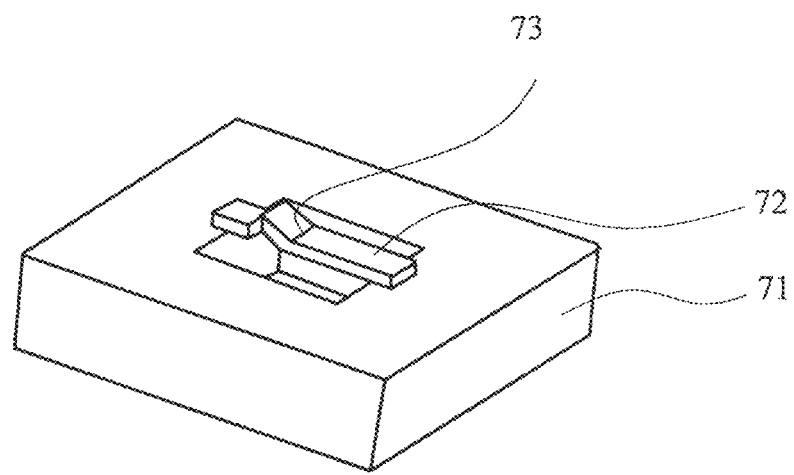
FIGS. 7A and 7B show various steps during the production of a microscopic specimen, which has two bending edges.
Figure 7B:
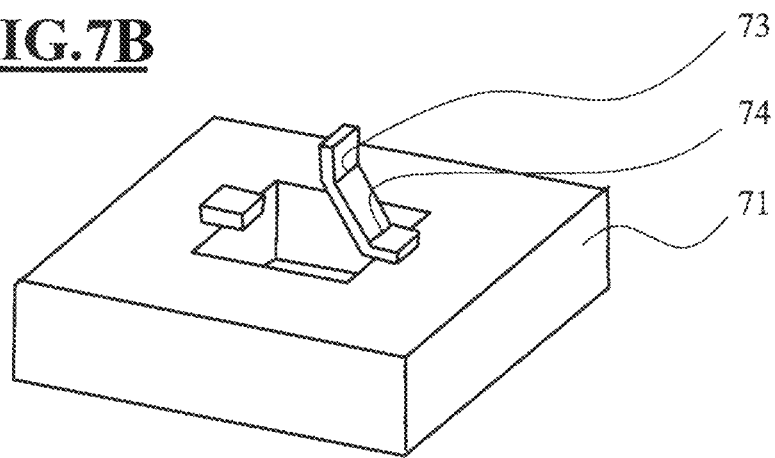

FIGS. 7A and 7B schematically show a further embodiment of the method according to the disclosure. In the specimen block 71 there is an exposed structure 72, which has a first bending edge 73. The structure 72 has been shaped along the first bending edge 73 using the method according to the disclosure. The shaped structure can now be shaped another time. A second bending edge 74 is produced by the action of the particle beam, and so the shaped structure 72 now has two bending edges 73, 74.

Figure 8A:
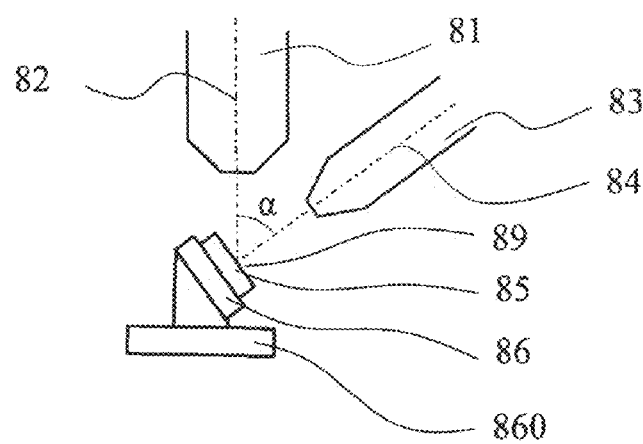
FIGS. 8A and 8B shows steps of a special method.
Figure 8B:
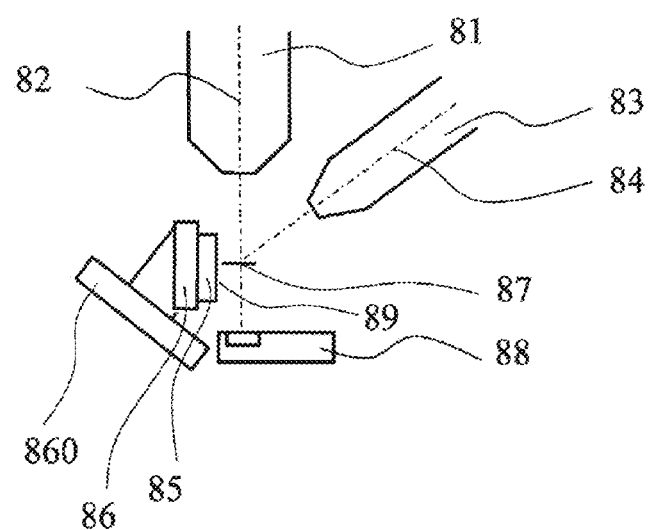

FIGS. 8A and 8B illustrate a further, particularly advantageous configuration of the method in which a microscopic specimen is prepared in situ by the method according to the disclosure and the shaped exposed structure is examined using a STEM detector. A STEM (Scanning Transmission Electronic Microscopy) detector detects electrons that have passed through a specimen that is electron transparent at least at points, and it is usually attached to a scanning electron microscope or an SEM-FIB combination device.

It is particularly advantageous if this embodiment of the method is carried out using a two-beam device which includes a STEM detector 88. Such a two-beam device includes an electron beam column 81 and an ion beam column 83. Both columns 81, 83 each have an optical axis 82, 84, said axes adopting an angle α in relation to one another since the columns are arranged inclined with respect to one another. By way of example, the absolute value of the angle α can be 54°. However, it is also conceivable for the magnitude of the angle α to adopt a value in the range between 0° and 90° or between 10° and 90°. It can be particularly advantageous if the angle α adopts a value in the range from 40° to 80° or in the range from 45° to 70° or in the range from 50° to 60°, for example 52° or 55°.

A specimen block 85 with an exposed structure is received on the specimen receptacle 86, which is arranged at a specimen stage 89. The specimen receptacle 86 has a displaceable and rotatable (tiltable) embodiment. The axis of rotation of the specimen receptacle 86 extends perpendicular to a plane spanned by the optical axis 82 of the electron beam column and the optical axis 84 of the ion beam column. That is to say that the axis of rotation of the specimen receptacle 86 extends perpendicular to the plane of the drawing in the example of FIGS. 8A and 8B. Usually, the axis of rotation is also referred to as a tilt axis of the specimen receptacle 86. By way of a rotation about this tilt axis, the specimen receptacle 86 can adopt different angles in relation to the optical axes 82, 84. Moreover, it can be advantageous if the specimen receptacle 86 is arranged in rotational fashion in relation to the specimen stage 860 and consequently able to adopt different angles in relation to the base of the specimen stage 860.

Initially, the specimen receptacle is rotated in such a way that a first boundary surface 89 of the exposed structure extends substantially perpendicular to the optical axis 84 of the ion beam column 83. This means that the first boundary surface 89 is arranged in the focal plane of the ion beam column 83. This arrangement is advantageous in that the specimen block 85 can be processed by the ion beam and, at the same time, observed with the aid of the electron beam and a detector for detecting products of the interaction between electrons and specimen material.

When carrying out an observation using the STEM detector, it is advantageous if the specimen has a lamella-like form. A lamella is understood to mean a flat cuboid, the length and width extent of which is usually only a few micrometers (μm). The thickness (lamella thickness) of the cuboid should be selected to be such that the lamella is transmissive for electrons, and so the thickness is usually less than one hundred nanometers (nm).

The lamella is prepared in such a way that it is freed at the two sides, at the one end side and at the sides facing the specimen block. That is to say, the lamella (which represents the exposed structure) is only still connected to the specimen block at the second end side.

Now, a bending edge is produced in the exposed structure using the ion beam. Advantageously, the bending edge is produced in the, or at the, second end face that is still connected to the specimen block by virtue of specimen material being removed along a line. This leads to the exposed structure being shaped and bent out of the focal plane of the ion beam in the direction toward the ion beam. Should the region of interest of the lamella not be electron transparent yet or not be sufficiently electron transparent, this region can now be thinned with the ion beam until the region is sufficiently thin.

Then, the specimen receptacle 86 with the specimen block 85 is rotated and—should this be desired—modified in terms of its spatial position such that the shaped exposed structure 87 is positioned perpendicular to the optical axis 82 of the electron beam column 81.

The specimen region of interest in the shaped structure 87 is now penetrated by electrons from the electron beam column 81. In relation to the propagation direction of the electrons, the STEM detector 88 is arranged downstream of the specimen, and so the interaction products that arose when the specimen was penetrated can be detected by the STEM detector 88. Advantageously, the STEM detector 88 is configured in such a way that it can be inserted into the specimen chamber for use and can be retracted therefrom again after use.

Advantageously, the various embodiments of the method according to the disclosure can be carried out with a two-beam device (FIB-SEM combination device) with the gas injection system, which is illustrated in FIG. 9. The two-beam device 91 includes two particle beam columns, namely an electron beam column 93 for producing an electron beam and an ion beam column 108 for producing an ion beam. Both particle beams are directed to the processing location on the specimen 103, which advantageously is situated at the coincidence point of both particle beams. The specimen 103 is received in a specimen receptacle 104 and situated in the specimen chamber 92 of the two-beam device, in which vacuum conditions are prevalent.

Advantageously, the specimen receptacle 104 is embodied as a five-axis specimen stage. This means that the specimen receptacle 104 can be displaced in the x-, y- and z-direction—i.e., in three mutually perpendicular spatial directions—and can be rotated about a tilt axis and an axis of rotation. The rotation about the tilt axis, which extends perpendicular to a plane spanned by the optical axes 96, 107 (i.e., perpendicular to the plane of the drawing), renders it possible to allow the surface of the specimen, which is intended to be irradiated by charged particles, to adopt different adjustable angles in relation to the optical axes 96, 107.

During operation, primary electrons are produced in the electron source 94, said primary electrons being accelerated along the optical axis 96 of the electron beam column 93, focused by the lens-element systems 95, 97 and trimmed by at least one aperture stop 98. Moreover, the electron beam column 93 includes a deflection system 99, via which the primary electron beam can be guided over the specimen 103 in a raster-type manner. Furthermore, the FIB-SEM combination device 91 includes at least one detector 100 for detecting interaction products of the interaction between particle beam and specimen 103.

Moreover, the two-beam device 91 includes an ion beam column 108 with an ion source 109, a deflection system 106 and a focusing lens element 105. The ions produced in the ion source 109 are accelerated along the optical axis 107 of the ion beam column 108 and focused such that the ions are incident on the specimen 103 in focus and can be used to ablate material from the specimen 103 and/or image the specimen.

It is advantageous if the particle beam device moreover has a gas injection system (GIS) 102. The latter usually includes a reservoir for a process gas which can be supplied in a controlled fashion to the specimen 103 via a line that ends near the processing location. The process gas can be embodied as a precursor gas. The precursor gas is initially activated by the ion beam or the electron beam and thus converted into a reactive form that is able to ablate specimen material or deposit material at the specimen. By way of example, a precursor gas of xenon difluoride (XeF$_2$) can be supplied, which is converted into the reactive xenon difluoride by activation such that the specimen material is etched. The processing progress of the specimen can be simultaneously or successively observed with the aid of the electron beam column 93 and a connected detector 100.

Moreover, the particle beam device 91 includes an evaluation and control unit 101. The evaluation and control unit 101 can carry out a sequence of control commands, which are included in a computer program product. By carrying out the control commands, the particle beam device is prompted to carry out the method according to the disclosure.

Figure 10A:
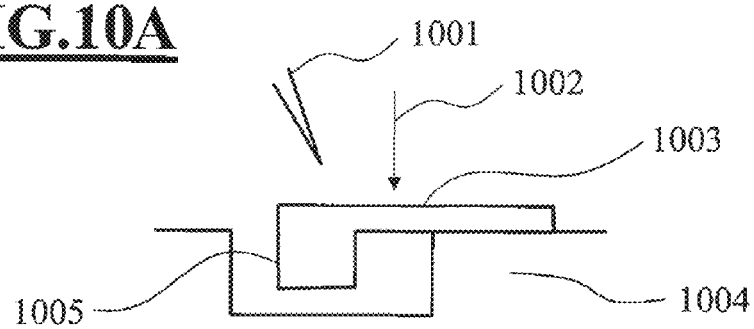
FIGS. 10A-10D schematically show steps of a special method.
Figure 10B:
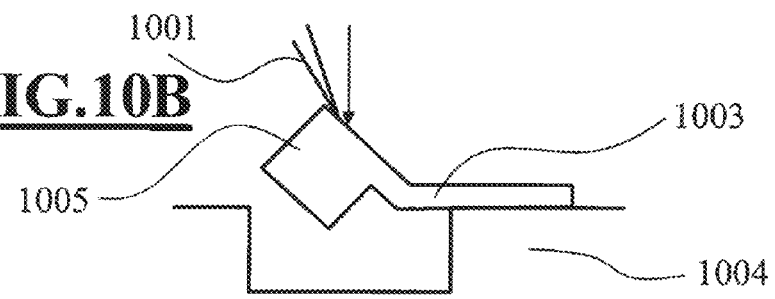
Figure 10C:
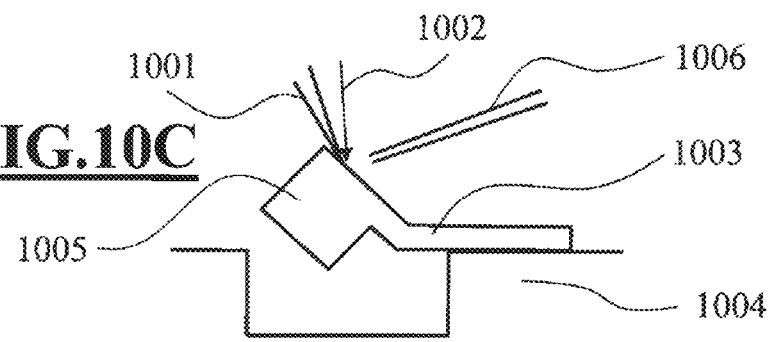
Figure 10D:
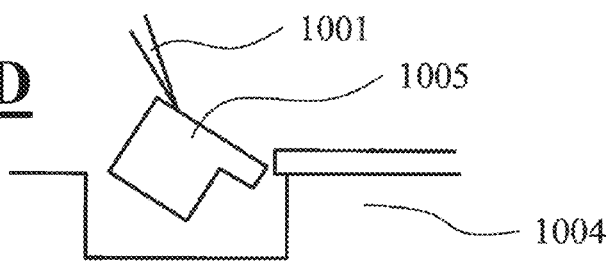

In a special embodiment, which is illustrated in FIGS. 10A-D, the method can be used for the sparing transfer of a prepared specimen onto a manipulator needle 1001 or a specimen carrier. To this end, the particle beam device includes a displaceable transfer apparatus, which advantageously includes a micromanipulator, which has a manipulator needle 1001 or a similar tool for receiving the specimen. The exposed, i.e., cantilever- shaped, specimen 1003 is shaped as described above by the action of the particle beam 1002 (FIG. 10A). In the process, the exposed structure and, therewith, the specimen region of interest 1005 move in the direction of the manipulator needle 1001 until the exposed structure contacts the manipulator needle 1001. This is advantageous in that the user notices when the specimen material in fact abuts the manipulator needle 1001, specifically when the shaping movement is stopped on account of the resistance of the micromanipulator needle 1001 (FIG. 10B). The force exerted on the specimen material in the process is very low, and so there is no damage. By contrast, specimens are often damaged in conventional methods by the movement of the manipulator needle. Subsequently, the shaped structure is fastened to the manipulator needle 1001 (FIG. 10C). By way of example, this can be effected by a gas-assisted deposition of platinum-containing layers with the ion or electron beam (FIG. 10C). To this end, a precursor substance is applied to the manipulator needle 1002 and the specimen material 1003, for example with the aid of a hollow needle 1006, and converted into material that is deposited with the aid of the particle beam 1002. Then, the exposed structure 103 is severed from the specimen block 1004 (FIG. 10D) such that the specimen region of interest 1005 can now be moved into any position by displacing the manipulator needle 1001.

By way of example, the specimen transferred in this manner can be a TEM lamella, a microscopic tomography specimen or the conductor track of an electronic component. Advantageously, the employed particle beam device includes an ion beam column for producing a focused ion beam. It is particularly advantageous if the particle beam device is embodied as a multi-beam device, which includes an ion column for producing a focused ion beam and an electron column for producing a focused electron beam. It is also conceivable for the particle beam device to include a gas injection system for introducing etching gas such that the structure can be processed via gas-assisted etching or that coatings can be deposited.

It is also conceivable for a specimen region of interest to be transferred onto a specimen carrier, for example a glass tip or a micromanipulator needle, with the aid of the method according to the disclosure. To this end, a specimen carrier is introduced into the specimen chamber via a micromanipulator and held above the structure prepared to be free, which includes the specimen region of interest. By shaping the exposed structure according to the disclosure, the structure is moved in the direction of the specimen carrier until the structure abuts the specimen carrier and fastened to the specimen carrier by way of a gas-assisted deposition of platinum-containing layers, for example. Then, the specimen carrier can be brought into another position together with the specimen region of interest, or it can be transferred into another apparatus. It can be particularly advantageous if the specimen carrier has a cutout and the exposed structure is shaped in such a way that the region of interest is positioned in the cutout.

The methods described for transferring the specimen are advantageous in that the user can notice with some certainty when the specimen abuts on the micromanipulator needle or the specimen carrier, specifically when the resistance of the needle or of the specimen carrier stops the shaping movement. Moreover, only small forces act on the specimen such that the risk of damaging the specimen is minimized, and therefore this method is suitable for very sensitive specimens, too.

LIST OF REFERENCE SIGNS

S1 Step: Providing a specimen block
S2 Step: Producing a bending edge
S3 Step: Moving the specimen receptacle
S4: Step: Observing and/or processing the shaped structure
21 Particle-optical column
22 Optical axis
23 Focused particle beam
24 Observation and processing plane
25 Exposed structure
26 Specimen block
27 Shaped exposed structure
28 Bending edge
29 Particle beam for the further examination
280 Processing line
31 Specimen block
32 Specimen detail of interest
33 Exposed structure
34 Particle beam
35 Bending edge
36 Boundary surface (sectional view)
37 Cylindrical structure
38 Conical structure
41 Specimen block
42 Coating
43 Ablated region
44 Exposed structure
45 Severing cut
46 Shaped exposed structure
47 Bending edge
48 Particle
51 Specimen block
52 Exposed structure
53 Bending edge
61 Specimen block
62 Initial structure
63 Exposed structure
64 Bending edge
65 Three-dimensional object
71 Specimen block
72 Shaped exposed structure
73 First bending edge
74 Second bending edge
81 Electron beam column
82 Optical axis of the electron beam column
83 Ion beam column
84 Optical axis of the ion beam column
85 Specimen block
86 Specimen receptacle
87 Shaped exposed structure
88 STEM detector
89 First boundary surface
860 Specimen stage
91 Particle beam device
92 Specimen chamber
93 Electron beam column
94 Electron source
95 First condenser lens element system
96 Optical axis of the electron beam column
97 Second condenser lens element system
98 Aperture stop
99 Deflection system
100 Detector
101 Control and deflection unit
102 Gas injection system
103 Specimen block
104 Specimen receptacle
105 Focusing lens element
106 Deflection system
107 Optical axis of the ion beam column
108 Ion beam column
109 Ion source
1001 Micromanipulator needle
1002 Particle beam
1003 Cantilever-shaped structure
1004 Specimen block
1005 Specimen region of interest (ROI)
1006 Hollow needle

What is claimed is:

1. A method for in situ preparation of a microscopic specimen, using a particle beam device comprising a particle beam column to produce a focused beam of charged particles, a specimen receptacle to receive a specimen block, and a detector to detect interaction products of the interaction between particle beam and specimen material, the method comprising:
   providing a specimen block having a structure that is exposed and that comprises a specimen region of interest;
   using the particle beam to produce a bending edge in the exposed structure so that at least some of the exposed structure is shaped in a direction of the incident particle beam; and
   moving the specimen receptacle, in which the specimen block is received, so that a specimen region, which is enclosed by the shaped structure, is observable and/or processable in the particle beam device.

2. The method of claim 1, further comprising observing and/or processing the specimen region of interest with the aid of the particle beam device.

3. The method of claim 1, wherein producing the bending edge comprises predetermining a desired size of the shape of the exposed structure and producing the desired shape.

4. The method of claim 1, wherein producing a bending edge is repeated so that the microscopic specimen has a plurality of bending edges.

5. The method of claim 1, further comprising stabilizing the form of the bending edge by applying a deposition.

6. The method of claim 1, wherein the particle beam device comprises an ion beam column, and the particle beam comprises a focused ion beam.

7. The method of claim 1, wherein the particle beam device comprises a multi-beam device, which comprises an ion beam column that produces a focused ion beam and an electron beam column that produces a focused electron beam.

8. The method of claim 1, wherein:
the particle beam device comprises an electron beam column that produces a focused electron beam and a gas injection system that introduces etching gas; and
the electron beam and etching gas produce the bending edge.

9. The method of claim 1, wherein providing the exposed structure comprises depositing a coating.

10. The method of claim 9, wherein the coating comprises platinum.

11. The method of claim 10, wherein the exposed structure is exposed from the specimen block by etching.

12. The method of claim 11, further comprising supplying an XeF2-precursor for etching purposes.

13. The method of claim 10, wherein:
a specimen block is provided, in which the specimen region of interest has a particle that is situated on the surface of the specimen block;
by applying a deposition, the particle is embedded in the deposition material;
the deposition is undercut in etching such that the deposition with the particle forms the exposed structure; and
the bending edge is produced in the deposition.

14. The method of claim 1, wherein the microscopic specimen comprises a TEM lamella.

15. The method of claim 1, wherein the microscopic specimen comprises a tomography specimen.

16. The method of claim 1, wherein the exposed structure comprises a conductor track of an electronic component.

17. The method of claim 1, wherein:
the particle beam device comprises an electron beam column and a STEM detector;
the specimen region of interest is transparent to electrons; and
the method further comprises:
passing electrons from the electron beam column through the specimen region of interest; and
using the STEM detector to detect interaction products arising as a result thereof.

18. One or more machine-readable hardware storage devices comprising instructions that are executable by one or more processing devices to perform operations comprising:
performing the method of claim 1.

19. A method for transferring a microscopic specimen, carried out using a particle beam device comprising a particle beam column for producing a focused beam of charged particles; a specimen receptacle for receiving a specimen block; a detector for detecting interaction products of the interaction between particle beam and specimen material; and a displaceable transfer apparatus for receiving the microscopic specimen, the method comprising:
providing a specimen block having a structure that is exposed and that comprises the specimen to be prepared;
positioning the transfer apparatus;
using a particle beam to form a bending edge in the exposed structure so that at least some of the exposed structure is shaped in a direction of the incident particle beam, wherein the shaped structure is moved into a vicinity of the transfer apparatus;
fastening the structure to the transfer apparatus; and
severing the structure from the specimen block.

20. One or more machine-readable hardware storage devices comprising instructions that are executable by one or more processing devices to perform operations comprising:
performing the method of claim 19.

* * * * *

UNITED STATES PATENT AND TRADEMARK OFFICE
CERTIFICATE OF CORRECTION

PATENT NO. : 10,347,461 B2
APPLICATION NO. : 16/022230
DATED : July 9, 2019
INVENTOR(S) : Andreas Schmaunz and Holger Doemer Page 1 of 1

It is certified that error appears in the above-identified patent and that said Letters Patent is hereby corrected as shown below:

In the Specification

Column 2, Lines 10-14, Delete "the microscopic specimen is severed from the specimen block, whereas this occurs within the FIB device in the in situ methods. What is common to both methods is that special manipulation tools such as micromanipulators, micro grippers or needles are involved." and insert the same on Column 2, Line 9, as a continuation of same paragraph.

Column 2, Line 53, Delete "Rösier" and insert -- Rösler --, therefor.

Signed and Sealed this
Twenty-second Day of October, 2019

Andrei Iancu
*Director of the United States Patent and Trademark Office*